United States Patent [19]

Van Iten

[11] Patent Number: 5,350,371
[45] Date of Patent: Sep. 27, 1994

[54] CATAMENIAL TAMPON

[75] Inventor: Thomas P. Van Iten, Neenah, Wis.

[73] Assignee: Kimberly-Clark Corporation, Neenah, Wis.

[21] Appl. No.: 14,071

[22] Filed: Jan. 29, 1993

Related U.S. Application Data

[63] Continuation of Ser. No. 798,371, Nov. 26, 1991, abandoned.

[51] Int. Cl.$^5$ .................. A61F 13/15; A61F 13/20
[52] U.S. Cl. ................... 604/398; 604/358; 604/367; 604/374; 604/379; 604/385.1; 604/904; 604/11; 604/13
[58] Field of Search .................. 604/11–15, 604/358, 367, 374, 378–380, 384, 385.1, 904

[56] References Cited

U.S. PATENT DOCUMENTS

| | | | |
|---|---|---|---|
| 1,224,735 | 5/1971 | Gamache et al. | |
| 2,529,183 | 11/1950 | Parish | 604/904 |
| 2,553,000 | 5/1951 | Parish | 604/904 |
| 2,652,056 | 9/1953 | Lay | 604/904 |
| 2,815,756 | 12/1957 | Graham, Jr. | 604/904 |
| 2,926,394 | 3/1960 | Bletzinger et al. | 604/904 |
| 3,063,453 | 11/1962 | Brecht | |
| 3,340,874 | 9/1967 | Burgeni | |
| 3,683,912 | 8/1972 | Olson et al. | 604/904 |
| 3,765,417 | 10/1973 | Crockford | |
| 3,854,481 | 12/1974 | Messing | |
| 4,027,673 | 6/1977 | Poncy | 604/904 |
| 4,755,166 | 7/1988 | Olmstead | |
| 5,047,024 | 9/1991 | Glassman | |
| 5,158,535 | 10/1992 | Paul et al. | |

FOREIGN PATENT DOCUMENTS

| | | | |
|---|---|---|---|
| 0530852 | 9/1956 | Canada | 604/379 |
| 0243250 | 10/1987 | European Pat. Off. | |
| 0422660A1 | 4/1991 | European Pat. Off. | |
| 1808848 | 6/1970 | Fed. Rep. of Germany | |
| 384249 | 4/1908 | France | |
| 523681 | 6/1972 | Switzerland | |

Primary Examiner—Randall L. Green
Assistant Examiner—P. Zuttarelli
Attorney, Agent, or Firm—Thomas J. Connelly; Mark L. Davis

[57] ABSTRACT

A catamenial tampon is disclosed for absorbing menstrual fluid. The tampon includes a compressed pledget having a major and a minor radius of curvature. Zones of different density fibers are arranged adjacent to each radius of curvature and the zones can extend substantially the entire length of the pledget. The pledget is constructed of absorbent fibers which are enclosed by a cover. A withdrawal string is attached to the pledget and facilitates removal of the tampon from a woman's vagina. The absorbent is compressed into an elongated, generally cylindrically shaped pledget having a zone of high density fibers and a zone of low density fibers. After compression, the low density fibers will expand and form a curved tampon.

22 Claims, 2 Drawing Sheets

CATAMENIAL TAMPON

This is a continuation of copending application(s) Ser. No. 07/798,371 filed on Nov. 26, 1991.

FIELD OF THE INVENTION

This invention relates to a catamenial tampon for absorbing menstrual fluid and, more particularly, to a curved tampon having zones of different density fibers which maintain the curvature of the tampon prior to use.

BACKGROUND OF THE INVENTION

Currently, there are two basic types of tampons used for feminine hygiene. The first type is a digital tampon which can be inserted into a woman's vagina by the user's fingers. The second type is a tampon retained in an applicator wherein the tampon is inserted into a woman's vagina via the applicator. Both types of tampons are commonly made by folding or rolling a loosely associated rectangular strip of absorbent material into a blank and then compressing the blank into a cylindrically shaped product known as a pledget. The pledget may or may not have a cover. In both types of tampons, a withdrawal string is attached to the pledget to provide a means for removing the tampon from the woman's vagina. In the applicator style tampon, the tampon is normally assembled into the applicator prior to being wrapped and packaged.

Until now, most tampons have been manufactured having a straight cylindrical profile. Representative samples of such tampons are taught in U.S. Pat. Nos. 3,340,874; 3,854,481 and 5,047,024. A disadvantage of a straight profile is that, in the female body, the vaginal cavity is curved, and a woman can experience discomfort when trying to insert a straight tampon into her vagina.

There are patents which teach the use of a curved applicator or stick to facilitate insertion of a straight tampon into a woman's vagina. U.S. Pat. Nos. 1,224,735 and 4,755,166 are representative. However, these various types of applicators still utilize a straight tampon. U.S. Pat. No. 3,765,417 issued to Crockford, and assigned to the present assignee, is one patent which does teach a tampon having an arcuate shape which is designed to be utilized with a curved applicator. This curved tampon is formed from folding a sheet of compressed, absorbent material and has a slight curvature. However, no mention is made to forming a curved tampon, having a generally cylindrical shape, which could be inserted without an applicator. Furthermore, Crockford does not teach a curved tampon having zones of different density fibers which maintain the curvature of the tampon prior to use.

Now, a catamenial tampon has been developed which is curved to correspond to the curvature of a woman's vagina. The tampon can be easily inserted into a woman's vagina without discomfort and has zones of different density fibers which maintain the curvature of the tampon prior to use.

SUMMARY OF THE INVENTION

Briefly, the present invention relates to a catamenial tampon for absorbing menstrual fluid. The tampon includes a compressed pledget having a major and a minor radius of curvature. The pledget has zones of different density fibers arranged adjacent to the major and minor radii of curvature. The zones of different densities can extend substantially along the entire length of the pledget. The pledget is constructed from an absorbent optionally enclosed by a nonwoven cover. A withdrawal string is attached approximate one end of the pledget. The withdrawal string is used to remove the tampon from the vagina after the tampon has absorbed menstrual fluid. The absorbent is compressed into an elongated, generally cylindrically shaped pledget having a zone of high density fibers and a zone of low density fibers. After compression, the low density fibers will expand and form a curved tampon.

The general object of this invention is to provide a catamenial tampon for absorbing menstrual fluid. A more specific object of this invention is to provide a catamenial tampon having a curved or arcuate shaped pledger.

Another object of this invention is to provide a catamenial tampon having a curved pledger which is rigid and self sustaining prior to use.

Still another object of this invention is to provide a curved tampon which closely approximates the curvature of a woman's vagina and is rigid enough to be employed as a digital tampon.

Still further, an object of this invention is to provide a curved tampon which is easier to insert into a woman's vagina than a straight tampon.

Other objects and advantages of the present invention will become more apparent to those skilled in the art in view of the following description and the accompanying drawings.

DETAILED DESCRIPTION OF THE PREFERRED EMBODIMENTS

Figure 1:
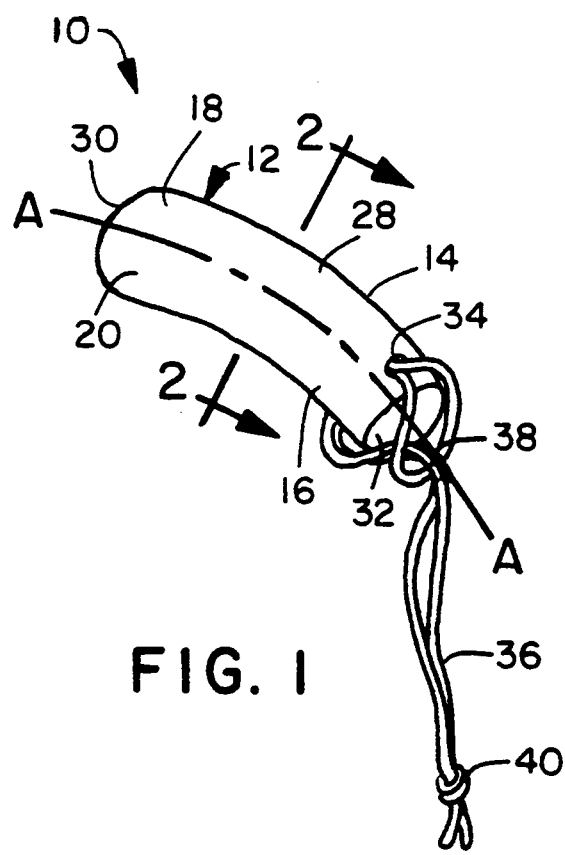
FIG. 1 is a perspective view of a catamenial tampon having a compressed pledget with a major and a minor radius of curvature and having a zone of low density fibers located adjacent to the major radius of curvature and a zone of high density fibers located adjacent to the minor radius of curvature.

Referring to FIG. 1, a catamenial tampon 10 is shown which is capable of absorbing menstrual fluid, blood, etc. during a woman's menstrual period. The tampon 10 includes a compressed pledget 12 having a central longitudinal axis labeled A—A. The central longitudinal axis A—A is flanked by a major radius of curvature 14 and a minor radius of curvature 16. The central longitudinal axis A—A can be formed on an arc having a radius of curvature of about 3-8 inches (76.2-302.2 mm), preferably about 4-7 inches (101.6-177.8 mm). The major and minor radii of curvature, 14 and 16 respectively, are located on opposite sides of the longitudinal axis A—A. The major radius of curvature is formed on a radius which is larger than the radius on which the minor radius of curvature is formed. Another way of defining the radii of curvature 14 and 16 is that an arc forming the longer outer surface of the tampon 10 is the major radius of curvature 14 and an arc forming the shorter outer surface of the tampon 10 is the minor radius of curvature 16.

The pledget 12 can be formed from any suitable absorbent material made from natural or artificial fibers, including: cotton, polyester, cellulose, acetate, nylon, polypropylene, rayon or blends thereof. The absorbent can also be a nonwoven, bonded carded web comprised of cotton and rayon fibers. A homogeneous blend of about 50–75 percent bleached cotton linter fibers and about 25–50 percent rayon fibers works well. When a cotton and rayon blend is utilized, the cotton fibers can be of various denier and can be of different lengths. The moisture content of the cotton fibers should be in the range of about 10–15 percent. The rayon fibers should have a denier of about 3–8, a staple length of about 1–2 inches (25.4–50.8 mm) and they should also possess high crimp properties. The rayon fibers should most likely have a dull finish. The moisture content of the rayon fibers should be in the range of about 10–12 percent.

Figure 2:
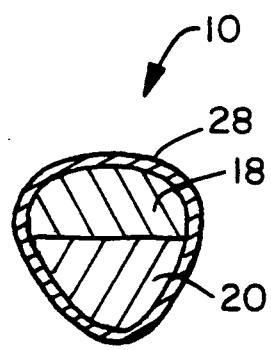
FIG. 2 is a cross-sectional view of the catamenial tampon shown in FIG. 1 taken along line 2—2.

Referring to FIG. 2, the pledget 12 contains at least two zones of different density fibers 18 and 20. A zone of low density fibers 18 is arranged adjacent to the major radius of curvature 14, and a zone of high density fibers 20 is arranged adjacent to the minor radius of curvature 16. Each zone, 18 and 20, occupies at least about 25 percent of the volume of the pledget 12 and, preferably, occupies at least 40 percent of the volume of the pledger 12. Most preferably, the zone of low density fibers 18 occupies about 60 percent of the volume of the pledget 12, while the zone of high density fibers 20 occupies about 40 percent of the volume of the pledget 12. It should be noted that the particular percent of each zone can vary upon one's particular tampon design and/or manufacturing process.

Referring again to FIG. 1, the zones 18 and 20 can extend substantially the entire length of the pledget 12 and can be aligned adjacent to one another. However, if desired, the zones 18 and 20 can extend over only a portion of the entire length of the pledget 12. For example, the zones 18 and 20 can extend over only the central portion of the pledget 12.

Figure 3:
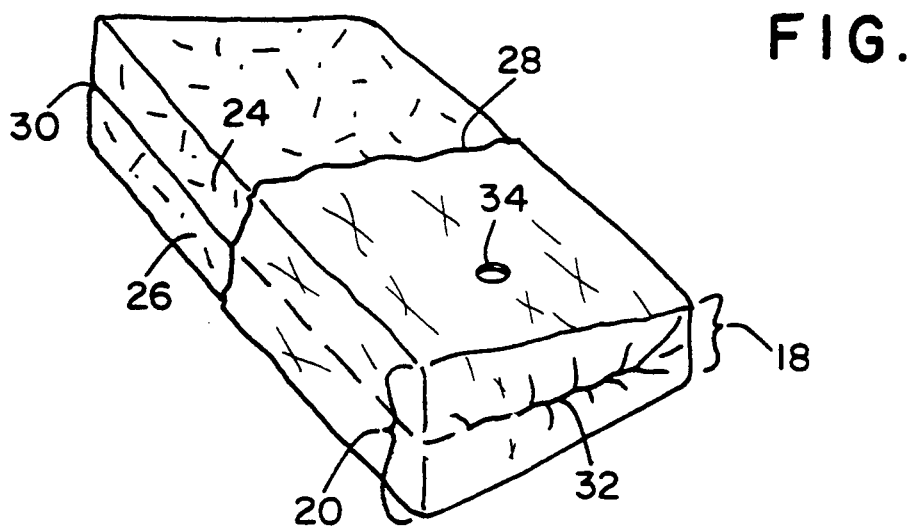
FIG. 3 is a perspective view of a wedge-shaped absorbent which can be used to construct the curved tampon.

Referring to FIG. 3, an absorbent 22 having a varying thickness is depicted. The absorbent 22 is shown having a wedge-shaped, cross-sectional configuration and is formed by joining two absorbent layers 24 and 26 together. However, it should be noted that the absorbent 22 could be formed from a single sheet of fibers. The absorbent 22 has an overall length of between about 2.5–4.0 inches (63.5–101.6 mm), a width of between about 1–2 inches (25.4–50.8 mm), and a thickness which ranges from between about 0.5 to 1.5 inches (12.7–38.1 mm) at its thickest point to a thickness of between about 0.125 to 0.5 inches (3.2–12.7 mm) at its narrowest point. The zone of high density fibers 20 will correspond to the thicker portion of the absorbent 22 and will contain a greater volume of fibers than the zone of low density fibers 18. The zone of low density fibers 18 corresponds to the thinnest portion of the absorbent 22.

The absorbent 22 can optionally be enclosed by a cover 28. The cover 28 can be formed from a nonwoven material such as a polyolefin, particularly polypropylene or polyethylene. A preferred material is spunbond. The cover 28 is beneficial in assuring that the fibers of the absorbent 22 do not directly contact the inner walls of a woman's vagina. This assures that no fibers will be left behind in the vagina after the tampon 10 has been removed. The cover 28 can be tucked into distally spaced ends 30 and 32 of the absorbent 22 so as to completely surround and enclose the absorbent fibers. The cover 28 can also be constructed from a heat-sealable material to assist in bonding it to the absorbent 22, such as by heat and/or pressure.

An opening 34 can be formed through both the cover 28 and the absorbent 22 so as to provide a means for attaching a withdrawal string 36, see FIG. 1. The opening 34 is normally aligned perpendicular to the central longitudinal axis A—A of the pledget 12. The withdrawal string 36 is preferably attached to the absorbent 22 before it is compressed into the pledget 12. The opening 34 should be located close to the distal edge 32. This will enable the withdrawal string 36 to be inserted through the opening 34 and looped upon itself at 38. A knot 40 can then be formed near the free ends of the withdrawal string 36 to assure that the string 36 does not separate from the absorbent 22. The withdrawal string 36 provides a means for removing the tampon 10 from the woman's vagina after the tampon has absorbed a certain amount of menstrual fluid.

The front or insertion end 30 of the pledget 12 can be rounded to facilitate insertion into a woman's vagina, while the opposite end 32 is relatively flat. The rounding of the insertion end 30 is normally done during the compression of the absorbent 22. The rounding of the insertion end 30 is optional but is generally preferred by the consumer.

Referring again to FIG. 3, the absorbent 22 is shown before the withdrawal string 36 has been attached and before compression. In the typical manufacturing process, the withdrawal string 36 would be attached to the absorbent 22 before the absorbent 22 is subjected to compression. The absorbent 22 can be compressed in an elongated, cylindrical mold cavity while at a moisture content of between about 5–15 percent, preferably about 10–12 percent. The absorbent 22 can be subjected to an end compression force of between about 750–3,000 pounds per square inch, preferably between about 1,500–2,000 pounds per square inch. The pressure can be applied for a desired time period, generally for a period of time greater than 0.25 seconds, preferably from about 0.25–1.5 seconds. The resulting density of the compressed pledget 12 in the area of the minor radius of curvature can range from about 10–15 pounds per cubic foot at a moisture content of about 12 percent, while the density of the pledget 12 in the area of the major radius of curvature can range between about 6–10 pounds per cubic foot at a moisture content of about 12 percent.

The mold cavity can also be heated to an elevated temperature, for example, to a temperature of between about 50°–200° F. (10°–93.3° C.), preferably between about 90°–100° F. (32.2°–37.7° C.). Compression of the absorbent 22 yields an elongated, generally cylindrically shaped pledget 12. The pledger 12 will have an overall length of between about 1 and 1.5 inches (25.4–38.1 mm), preferably about 1.25 inches (31.75 mm), and can vary in diameter from about 0.30–0.75 inches (7.6–19.1 mm). The pledget 12 normally has a weight of between about 2.8 to 4.2 grams.

The pledger 12 is normally straight when it exits the mold cavity but quickly blossoms into a curved shaped pledget as is shown in FIG. 1. The curved shape is obtained by the expansion of the low density fibers in zone 18. The fibers in the high density zone 20 tend to retain their compressed shape and, therefore, do not expand, at least not to the same extent, nor as rapidly, as the fibers in the low density zone 18. The release or expansion of the low density fibers gives the tampon 10 its novel arcuate shape while maintaining a rigid configuration. The rigid configuration permits the tampon 10 to be utilized as a digital tampon which can be inserted into a woman's vagina without the assistance of an applicator.

It should be noted that, as the fibers of the low density zone 18 expand outward to give the tampon 10 its arcuate shape, the cross-sectional shape of the tampon 10 may vary from a true cylinder to more of a teardrop or oval-type configuration. The exact configuration which will be obtained will be dependent upon the type of fibers used, the amount the fibers are compressed, the moisture content of the fibers, the shape of the mold cavity, etc. Once the tampon 10 has been inserted into a woman's vagina, the tampon will absorb menstrual fluid, blood, etc., and the fibers in both the low and high density zones 18 and 20 will expand. This action will cause the tampon 10 to straighten out into a generally elongated, cylindrical shape.

Figure 4:
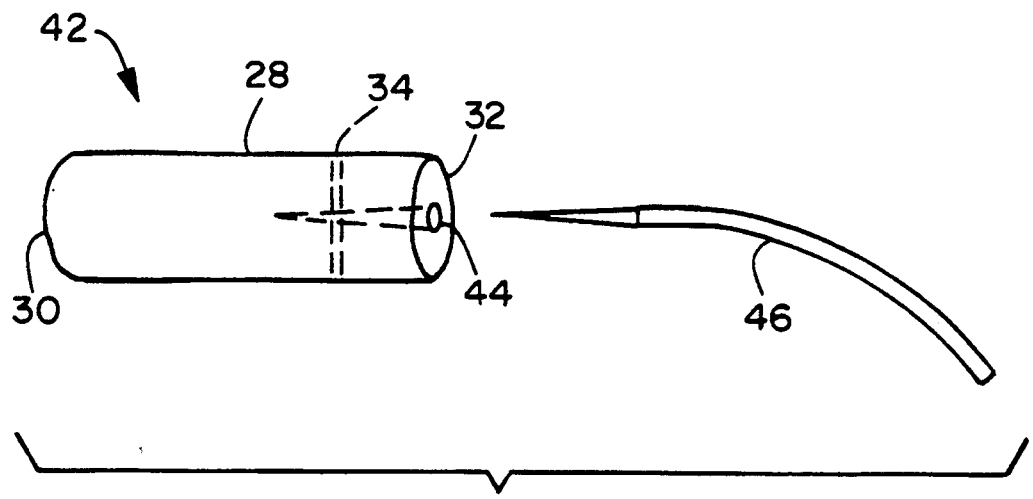
FIG. 4 is a perspective view of a compressed, generally cylindrically shaped pledger having an axial opening formed in an end thereof which can accommodate a stick.

Referring to FIG. 4, a compressed pledget 42 is shown having a rounded insertion end 30 and a flat opposite end 32. The pledget 42 is enclosed by a cover 28 and has an opening 34 formed radially therethrough for accommodating a withdrawal string 36. The pledget 42 also contains an axial opening 44 coaxially aligned with the central longitudinal axis A—A. The length of the opening 44 can be about 0.25-0.75 inches (6.35-19.5 mm), preferably about 0.625 inches (15.9 mm). The axial opening 44 can be formed, as the absorbent 22 is being compressed in the mold cavity, by inserting a pin into one end of the mold cavity. As the absorbent fibers are compressed around the pin, the opening 44 is formed. When the pin is removed, the opening 44 is exposed. The axial opening 44 is designed to accommodate the end of a stick 46. The stick 46 can be either straight or curved and, preferably, has a curve equal to the arc of the pledget 12. By using a curved stick having an arc similar to that of pledget 12, one can facilitate insertion of the tampon 10 into a woman's vagina in a comfortable fashion.

Figure 5:
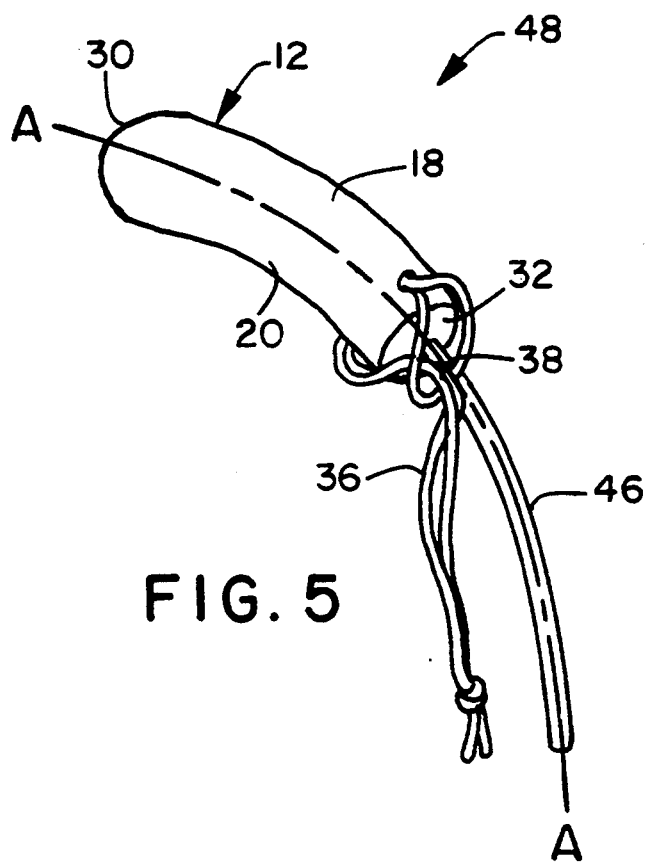
FIG. 5 is a schematic view of a curved tampon having a curved stick removably inserted into an opening formed in one end of the pledget for facilitating insertion of the tampon into a woman's vagina.

Referring to FIG. 5, a curved stick tampon 48 is depicted having a curved stick 46 which can assist a woman in positioning the tampon 10 into her vagina. Once the tampon 10 is inserted into the vagina, the stick 46 is withdrawn from the opening 44 and can be properly discarded.

Although not specifically shown in the figures, it should be noted that the curved tampon 10 can also be utilized with a curved applicator. The applicator can be constructed out of various materials, including: paper, cardboard, paperboard, plastic or other kinds of thermoplastic materials. An example of a curved tampon applicator is taught in U.S. Ser. No. 07/537,677 filed Jun. 14, 1990, to Paul et al. This patent application is incorporated by reference and made a part hereof.

While the invention has been described in conjunction with several specific embodiments, it is understood that many alternatives, modifications, and variations will be apparent to those skilled in the art in light of the aforegoing description. Accordingly, this invention is intended to embrace all such alternatives, modifications, and variations which fall within the spirit and scope of the appended claims.

I claim:
1. A tampon comprising:
   a) an absorbent curved slightly longitudinally along a central longitudinal axis prior to insertion into a woman's vagina, said absorbent having a length, and a major and a minor radius of curvature located on opposite sides of said longitudinal axis, said major and minor radii having zones of different fiber densities, said zones extending substantially along said length of said absorbent, wherein a cross section of said absorbent along said curved central longitudinal axis one of said zones is located directly adjacent to and above said axis and the other of said zones is located directly adjacent to and below said axis; and
   b) withdrawal string attached to said absorbent.
2. The tampon of claim 1 wherein a cover encloses said absorbent.
3. The tampon of claim 1 wherein said zone aligned adjacent to said minor radius of curvature has a greater density than said zone aligned adjacent to said major radius of curvature.
4. The tampon of claim 3 wherein said zone aligned adjacent to said minor radius of curvature has a greater volume of fiber than said zone aligned adjacent to said major radius of curvature.
5. A tampon comprising:
   a) an absorbent curved slightly longitudinally along a longitudinal axis prior to insertion into a woman's vagina, said absorbent having a length, and a major and a minor radius of curvature located on opposite sides of said longitudinal axis, said major and minor radii having zones of different density fibers, said zones extending substantially along said length of said absorbent, wherein a cross section of said absorbent along said curved central longitudinal axis one of said zones is located directly adjacent to and above said axis and the other of said zones is located directly adjacent to and below said axis;
   b) a cover enclosing said absorbent; and
   c) a withdrawal string attached to said absorbent.
6. The tampon of claim 5 wherein each of said zones occupies at least about 25% of a volume of said absorbent.
7. The tampon of claim 5 wherein said absorbent is comprised of a blend of about 50-75% cotton fibers and about 25-50% rayon fibers.
8. The tampon of claim 5 wherein said central longitudinal axis is formed on an arc having a radius of between about 3 to 8 inches.
9. The tampon of claim 5 wherein said central longitudinal axis is formed on an arc having a radius of between about 4 to 7 inches.
10. A curved tampon comprising:
    a) an absorbent formed from compressed cotton and rayon fibers, said absorbent curved slightly longitudinally along a central longitudinal axis prior to insertion into a woman's vagina, said absorbent having a major and minor radius of curvature located on opposite sides of said longitudinal axis, said major and minor radii having zones of different densities corresponding to each radius, said zones extending substantially along said length of said absorbent, wherein a cross section of said absorbent along said curved central longitudinal axis one of said zones is located directly adjacent to and above said axis and the other of said zones is located directly adjacent to and below said axis;

b) a cover enclosing said absorbent; and c) a withdrawal string attached to said absorbent.

11. The tampon of claim 10 wherein said absorbent includes a homogeneous blend of about 65-75% cotton fibers and about 25-35% rayon fibers.

12. The tampon of claim 10 wherein said zone arranged adjacent to said major radius of curvature has a density of between about 6-10 pounds per cubic foot at a moisture content of about 12 percent.

13. The tampon of claim 10 wherein said zone arranged adjacent to said minor radius of curvature has a density of between about 10-15 pounds per cubic foot at a moisture content of about 12 percent.

14. A tampon comprising:
a) an absorbent having a central longitudinal axis formed on an arc having a radius of between about 3-8 inches prior to insertion into a woman's vagina, said absorbent having a length, and a major and minor radius of curvature located on opposite sides of said longitudinal axis, said major and minor radii having zones of different density fibers corresponding to each of said radii of curvature, said zones extending substantially along said length of said absorbent, wherein a cross section of said absorbent along said curved central longitudinal axis one of said zones is located directly adjacent to and above said axis and the other of said zones is located directly adjacent to and below said axis;

b) a cover enclosing said absorbent; and c) a withdrawal string attached to said absorbent.

15. The tampon of claim 14 wherein said absorbent is comprised of two distinct wedge-shaped fibrous layers.

16. The tampon of claim 14 wherein said absorbent contains first and second distally spaced ends, said first end having a rounded tip.

17. The tampon of claim 16 wherein said cover completely encloses said absorbent and is tucked into said first and second ends.

18. The tampon of claim 14 wherein said absorbent has a weight of between about 2.8-4.2 grams.

19. A tampon comprising:
a) an absorbent curved slightly longitudinally along a central longitudinal axis prior to insertion into a woman's vagina, said absorbent having a length, and a major and minor radius of curvature with zones of different density fibers corresponding to each of said radii of curvature, said zones extending substantially along said length of said absorbent, wherein a cross section of said absorbent along said curved central longitudinal axis one of said zones is located directly adjacent to and above said axis and the other of said zones is located directly adjacent to and below said axis, said absorbent having distally spaced first and second ends, said second end having an opening formed therein;

b) a cover enclosing said absorbent;

c) a withdrawal string attached to said absorbent; and d) a stick removably inserted into said opening, said stick facilitating insertion of said tampon into said woman's vagina.

20. The tampon of claim 19 wherein said stick is curved.

21. A digital tampon comprising:
a) an absorbent curved slightly longitudinally along a central longitudinal axis prior to insertion into a woman's vagina, said absorbent having a major and a minor radius of curvature located on opposite sides of said longitudinal axis, said major and minor radii having zones of different densities, said zones extending substantially along said length of said absorbent, wherein a cross section of said absorbent along said curved central longitudinal axis one of said zones is located directly adjacent to and above said axis and the other of said zones is located directly adjacent to and below said axis; and b) withdrawing means for removing said absorbent.

22. A self-sustaining curved tampon comprising:
a) a compressed absorbent curved slightly longitudinally along a longitudinal axis prior to insertion into a woman's vagina, said absorbent having an outer periphery and at least two zones of different densities, said zones extending substantially along said length of said absorbent, wherein a cross section of said absorbent along said curved central longitudinal axis one of said zones is located directly adjacent to and above said axis and the other of said zones is located directly adjacent to and below said axis, each of said zones forming a portion of said outer periphery of said absorbent body; and b) withdrawal means for removing said absorbent.

* * * * *